United States Patent [19]

Leibinsohn

[11] Patent Number: 4,694,856

[45] Date of Patent: Sep. 22, 1987

[54] FLUID CONTROL DEVICE PARTICULARLY USEFUL IN LIQUID TRANSFUSION APPARATUS

[76] Inventor: Saul Leibinsohn, 11 Olei Hagardom Street, Rishon Lezion, Israel

[21] Appl. No.: 795,861

[22] Filed: Nov. 7, 1985

[30] Foreign Application Priority Data

Nov. 23, 1984 [IL] Israel .......................... 73598

[51] Int. Cl.⁴ .......................... F16K 7/06; A61M 5/16
[52] U.S. Cl. .......................... 137/555; 128/200.19;
137/601; 251/6; 251/7; 251/9; 604/251
[58] Field of Search .................. 137/599, 601, 552.5,
137/555, 599.1; 251/117, 4, 5, 6, 7, 8, 9;
604/250, 251, 246, 34; 128/40, 200.19

[56] References Cited

U.S. PATENT DOCUMENTS

| 485,698 | 11/1892 | Ketchum | 251/9 X |
|---|---|---|---|
| 2,649,112 | 8/1953 | Barnett et al. | 137/555 |
| 3,298,367 | 1/1967 | Bergman | 137/599 X |
| 4,373,524 | 2/1983 | Leibinsohn | 251/117 X |
| 4,458,877 | 7/1984 | Holmes | 251/117 |

FOREIGN PATENT DOCUMENTS

| 60004 | 3/1913 | Fed. Rep. of Germany | 137/555 |
|---|---|---|---|
| 540878 | 11/1941 | United Kingdom | 138/40 |

Primary Examiner—Martin P. Schwadron
Assistant Examiner—Stephen M. Hepperle

[57] ABSTRACT

A fluid control device for a liquid transfusion line comprises an inlet connector and an outlet connector, and a flexible conduit defining two, three or more passageways extending in parallel between them to provide a plurality of parallel paths for the flow of the fluid. The device further includes a restrictor in one or more but of the passageways restricting the flow according to a fixed predetermined rate lower than that of unrestricted passageway, and a manual control member for selectively closing the passageways to produce a flow of the fluid from the inlet connector to the outlet connector according to a preselected fixed rate.

3 Claims, 22 Drawing Figures

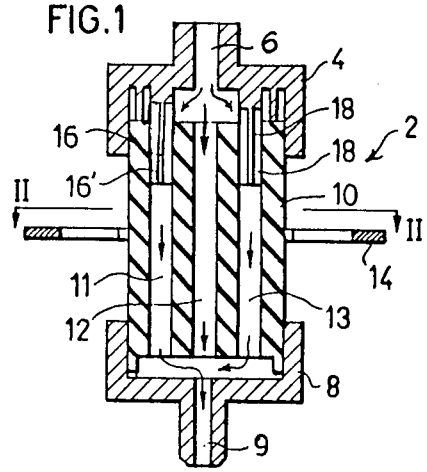
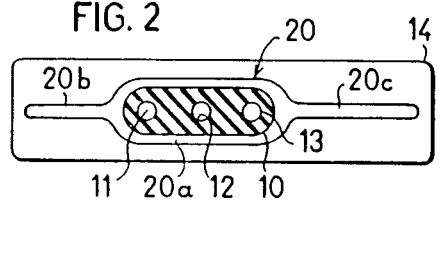
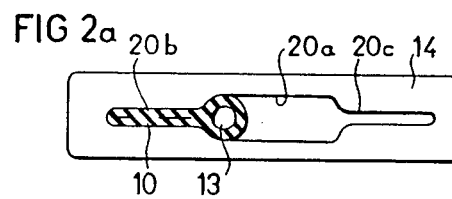
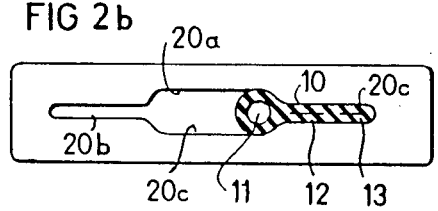
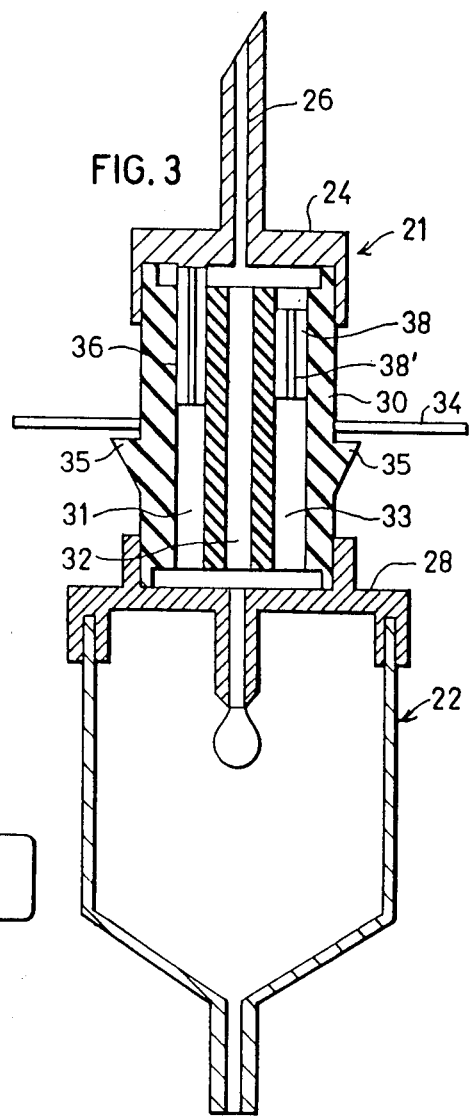

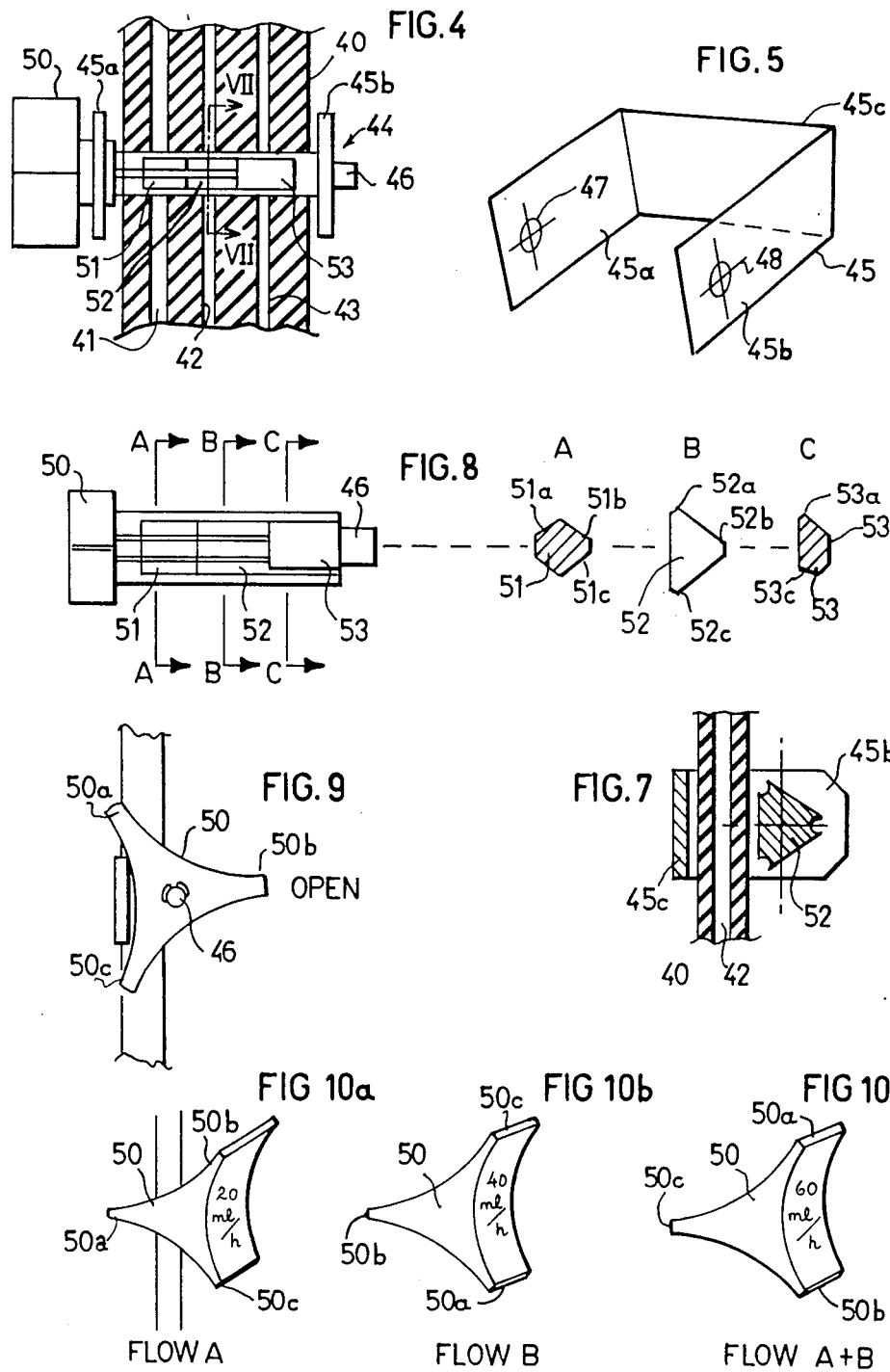

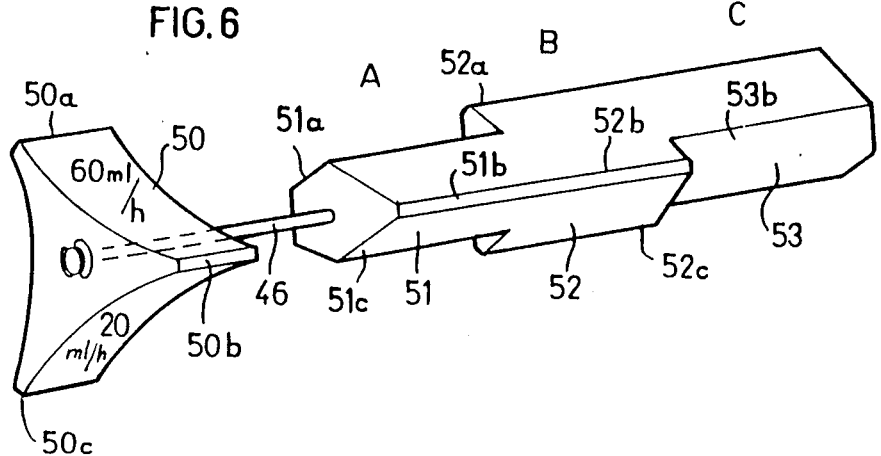
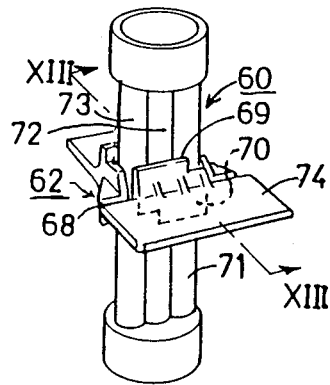
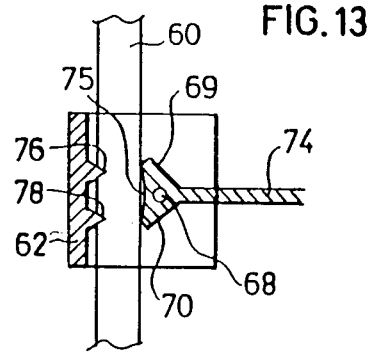
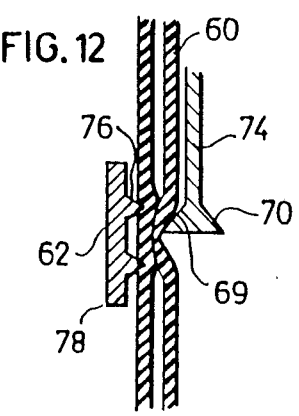
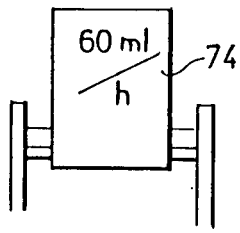

FIG. 15
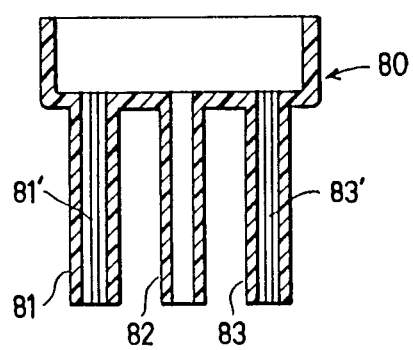
FIG 17
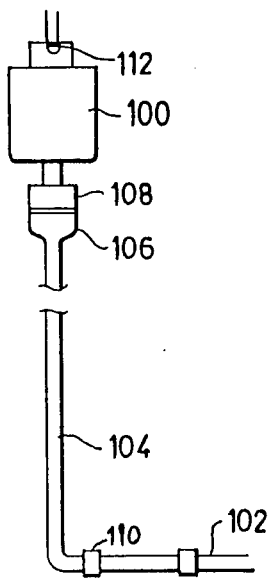
FIG. 16
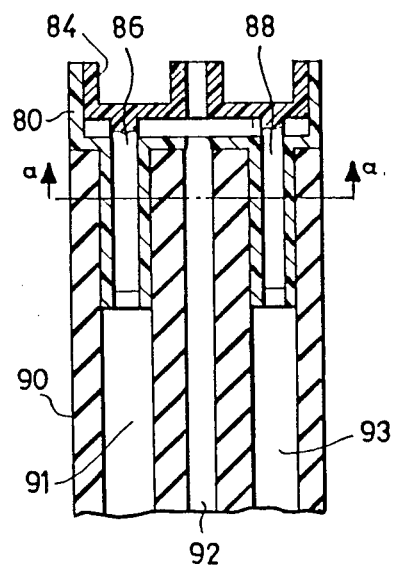
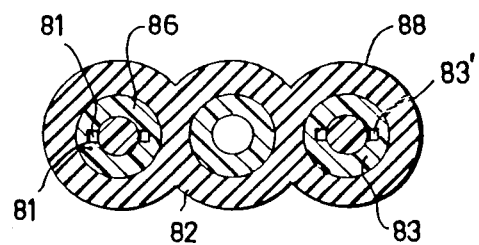
FIG 16α

FLUID CONTROL DEVICE PARTICULARLY USEFUL IN LIQUID TRANSFUSION APPARATUS

BACKGROUND OF THE INVENTION

The present invention relates to fluid flow control devices for controlling the flow of a fluid through a line. The invention is particularly useful in liquid transfusion apparatus for controlling the flow of the transfusion fluid, and is therefore described below with respect to this application.

The flow of a transfusion fluid must frequently be precisely controlled, and a number of devices have been developed for this purpose. However, the known techniques are usually of complicated construction which is costly to produce or difficult to preset and monitor.

An object of the present invention is to provide a fluid flow control device having advantages in the above respects. A particular object of the invention is to provide a fluid flow control device useful in a liquid transfusion system which device is of very simple construction and very easy to use.

SUMMARY OF THE INVENTION

According to a broad aspect of the present invention, there is provided a fluid flow control device conenctable in a line for controlling the flow of fluid therethrough, comprising: an inlet connector and an outlet connector; a flexible conduit defining at least two passageways extending in parallel between the inlet and outlet connectors to provide at least two parallel paths for the flow of the fluid there between; one of the passage ways having a full, unrestricted flow rate; a flow restrictor in at least one other of the passageways for restricting the flow therethrough according to a fixed predetermined rate lower than that of the other passageway; and a manually manipulatable control member for selectively closing said one or other passageway to produce a flow of the fluid from the inlet connector to the outlet connector according to a preselected fixed rate.

In the preferred embodiments of the invention described below, the flexible conduit includes three passageways extending in parallel between the inlet and outlet, two of the passageways including restrictors having different fixed flow rates. Accordingly, the control member may be manipulated to selectively close the passageways to preselect any one of three or more fixed flow rates.

Each restrictor, in the described preferred embodiment, is in the form of a cylindrical tube member receiving a cylindrical pin member, one of which members is formed with a recess extending a small fraction of its circumference to define a restricted passageway between the tube and pin members. In one described embodiment the recess is formed in the pin member, and in another described embodiment it is formed in the tube member.

BRIEF DESCRIPTION OF THE DRAWINGS

The invention is herein described, by way of example only, with reference to the accompanying drawings, wherein:

FIG. 1 is a longitudinal sectional view illustrating one form of fluid flow control device constructed in accordance with the present invention;

FIG. 2 is a sectional view along lines II—II of FIG. 1, illustrating a clamp used therein in its intermediate position for full fluid flow;

FIGS. 2a and 2b are views similar to that of FIG. 2 but illustrate the clamp in its two end positions for selecting one of two lower rates of flow;

FIG. 3 is a longitudinal sectional view illustrating a fluid flow control device incorporated in a liquid transfusion line;

FIG. 4 is a front elevational view illustrating a rotary type clamp useful in the device of FIGS. 1 and 3;

FIG. 5 is a three-dimensional view illustrating a part of the clamp of FIG. 4;

FIG. 6 is a three-dimensional view illustrating the rotary knob and cam shaft of the clamp of FIG. 4;

FIG. 7 is a sectional view along lines VII—VII of FIG. 4;

FIG. 8 is a diagrammatic view illustrating the configuration of the three sections in the cam shaft of FIG. 6;

FIG. 9 illustrates the fully open position of the clamp knob of FIG. 4;

FIGS. 10a, 10b and 10c, illustrate the positions of the clamp knob for three restricted flow rates;

FIG. 11 illustrates a pivotable type clamp that may be used in the device of FIGS. 1 or 3;

FIG. 12 is a sectional view along lines XII—XII of FIG. 11;

FIG. 13 illustrates another position of the pivotable cam member in the clamp of FIG. 11;

FIG. 14 illustrates the pivotable lever in the clamp of FIG. 11;

FIG. 15 is a three-dimensional view illustrating a metering collar which may be used in the fluid flow control devices described above;

FIG. 16 is a sectional view illustrating a part of the flow control device including the metering collar of FIG. 16;

FIG. 16a is an enlarged sectional view along lines a—a of FIG. 16; and

FIG. 17 illustrates a manner of locating the infusion bag of a liquid transfusion system at the required height to produce a predetermined flow rate.

DESCRIPTION OF PREFERRED EMBODIMENTS

The Embodiment of FIGS. 1 and 2

The fluid flow control device illustrated in FIG. 1 is particularly useful in a liquid transfusion system (FIGS. 3 and 17) in order to conveniently control the flow of the transfusion fluid according to preselected fixed rates. The device of FIG. 1, generally designated 2, comprises an inlet connector 4 at one end having an inlet 6 connectable to the tube leading to the transfusion bag, and at the opposite end an outlet connector 8 having an outlet 9 connectable to the feed tube for feeding the transfusion liquid to the patient. The flow control device 2 is inserted into the transfusion line upstream of the drip chamber commonly used in such liquid transfusion systems, as shown in FIG. 3.

The flow control device 2 illustrated in FIG. 1 further includes a flexible conduit 10 formed with three tubular passageways 11, 12, 13 extending in side-by-side relationship for the complete length of the conduit. Connectors 4 and 8 are constructed so that the liquid introduced via inlet 6 enters all three tubular passageways 11, 12 and 13, which passageways thus define three parallel paths for the liquid in its passage to outlet 9 of connector 8. Two of these passageways, namely passageways 11 and 13, include restrictors for restricting the flow therethrough according to a fixed predetermined rate; whereas the center passageway 12 does not include such a restrictor so that the fluid flows therethrough at the full, unrestricted and much higher rate. The device further includes a manually manipulatable control member 14 for selectively closing one or more of the passageways 11, 12 and 13 in order to control the flow of the fluid from inlet 6 to outlet 9 according to a preselected fixed rate.

In the embodiment illustrated in FIG. 1, the restrictors for tubular passageways 11 and 13 are shown at 16 and 18 respectively. Both are pins integrally formed with the inlet connector 4 so as to be received in the inlet ends of the respective passageways 11, 13. Each restrictor pin 16, 18 is formed with an axially-extending metering slit 16', 18' which, according to its dimensions, meters the flow of the liquid from inlet connector 4 through its respective passageway 11, 13. The dimensions of the two slits 16', 18' are different so as to provide two different flow rates.

Control member 14, as more particularly illustrated in FIG. 2, is of the shiftable clamp type which selectively closes one or more of the passageways by merely shifting it transversely of the passageways, i.e. left or right in FIGS. 1 and 2. Control member 14 thus includes a shaped slot 20 having a central section 20a of sufficiently large dimensions (length and width) to receive conduit 10 without pinching it. Slot 20 further includes two end sections 20b, 20c, on opposite sides of central section 20a. These end sections are of reduced width such as to pinch flexible conduit 20 to close one or more of its passageways 11–13 when received within one or the other of these end sections, as shown in FIGS. 2a and 2b, respectively.

The fluid flow control device illustrated in FIGS. 1 and 2 operates as follows:

When full flow is desired, clamp 14 is located in the position illustrated in FIG. 2, so as not to close any of the passageways 11, 12 and 13. Accordingly, the full (maximum) flow will be produced from the inlet 6 to the outlet 9.

If it is desired to reduce the flow rate to that determined by restrictor 18 in passageway 13, clamp 14 is shifted to the position illustrated in FIG. 2a wherein passageways 11 and 12 are received in the reduced-width section 20b of slot 20, thereby pinching closed these two passageways, and leaving only passageway 13 open. Accordingly, the rate of flow will be that determined by metering slot 18' of restrictor 18.

On the other hand, if it is desired to fix the flow rate according to that of restrictor 16 in passageway 11, clamp 14 is shifted to the position illustrated in FIG. 2b, wherein tubular passageways 12 and 13 are pinched closed by the slot end section 20c, thereby leaving only passageway 11 open for the flow of the fluid.

The Embodiment of FIG. 3

FIG. 3 illustrates a flow control device 21 similar to that of FIG. 2 included in a liquid transfusion line upstream of the drip chamber 22. Thus, the inlet connector 24 is formed with a spike 26 for connection to the transfusion bag, and the outlet connector 28 is integrally formed as the top wall of the drip chamber 22. In addition, the flexible conduit 30 formed with the three tubular passageways 31, 32, 33, further includes a ledge 35 for stably receiving the slidable clamp 34. In the FIG. 3 arrangement, restrictor 36 received within passageway 31 is integrally formed with the inlet connector 24 as in FIG. 1, but restrictor 38 received within passageway 33 is formed as a separate element inserted into that passageway. The latter feature permits inserts having different metering slots 38' to be inserted into passageway 33 in order to permit changes to be made in the fixed flow rate through that passageway.

The flow control device illustrated in FIG. 3 is otherwise constructed and operates in the same manner as described above with respect to FIGS. 1, 2, 2a and 2b.

The Embodiment of FIGS. 4–10c

FIGS. 4–10c illustrate another embodiment of the invention wherein the manipulatable flow control member is a rotary clamp, rather than a shiftable clamp.

FIG. 4 shows a portion of the flexible conduit, therein generally designated 40, having the three tubular passageways 41, 42 and 43, it being appreciated that restrictors (not shown) are provided at the upper ends of passageways 41 and 53 as in FIGS. 1 and 3. The clamp, generally designated 44, comprises a U-shaped holder 45 (FIG. 5) formed with a pair of parallel legs 45a, 45b joined by an intermediate leg 45c. A shaft 46 is rotatably supported in openings 47 and 48 in legs 45a, 45b.

Shaft 46 serves as a cam shaft having a multi-section cam in alignment with flexible conduit 40, and a knob 50 at one side of the flexible conduit.

Cam shaft 46 includes three cam sections, namely section 51 aligned with passageway 41, section 52 aligned with passageway 42, and section 53 aligned with passageway 43. Knob is of triangular shape; it is provided with three apices 50a, 50b and 50c, to indicate three different positions of the knob. The knob further includes indicia markings, as shown in FIGS. 10a, 10b and 10c, indicating three different fixed flow rate produced by each of the three positions of the knob. The different flow rates result from the configurations of the three cam sections 51–53 aligned with the respective passageways 41–43, so that the cam sections either open or close their respective passageways to produce the desired fixed flow rate according to the position of the cam shaft.

Thus, if knob 50 is positioned as illustrated in FIG. 10a, the flow rate is fixed for 20 ml/hr; this is indicated by the indicia facing the user in this position of the knob. In this position of the knob, flat surface 51a of cam section 51 faces its passageway 41, thereby non-obstructing this passageway; apex 52a of cam section 52 engages flexible conduit 40 to pinch its passageway 42 closed; and apex 53a of cam section 53 engages flexible conduit 40 to pinch its passageway 43 closed. Accordingly, only passageway 41 will be open, thereby producing a flow rate of 20 ml/hr.

When knob 50 is located in the position illustrated in FIG. 10b, apex 51b of cam section 51 pinches closed passageway 41; apex 52b of cam section 52 pinches closed passageway 42; but flat face 53b of cam section 53 permits that passageway to remain open, so that the flow will be only through passageway 43 at the fixed rate of 40 ml/hr, as indicated by the indicia viewable to the user in this position of knob 50.

When knob 50 is positioned as shown in FIG. 10c, flat face 51c of cam section 51 opens its passageway 41; apex 52c of cam section 52 closes its passageway 42; and flat face 53c of cam section 53 opens its passageway 43, so that the flow will be through both passageways 41 and 43 at the fixed rate of 60 ml/hr, as shown by the indicia viewable to the user when the knob is in this position.

FIG. 9 illustrates knob 50 in an intermediate position. There are three such intermediate positions, namely between each of the three above preset positions for producing fixed flow rates. In any of these three intermediate positions, all the cam sections 51, 52 and 53 will provide flat faces to flexible conduit 40 so that none of the three passageway 41, 42, 43 will be pinch closed, and therefore the flow rate will be very large. As shown particularly in FIGS. 6 and 8, the apices of the intermediate cam section 52 are flattened so as to stabilize knob 50 in these three preset positions of the knob. FIG. 7 illustrates a modification wherein they are of slightly concave configuration for this purpose.

The Embodiment of FIGS. 11–14

FIGS. 11–14 illustrate a still further embodiment of the invention wherein the flow control member is in the form of a pivotably mounted clamp which selectively produces any one of three fixed flow rates according to three pivoted positions of the clamp with respect to the flexible conduit, therein designated 60. For this purpose, the clamp includes a holder 62 pivotably mounting about axis 68 two cam sections 69 and 70 cooperable with the three passageways 71, 72, 73, corresponding to passageways 11, 12, 13 (FIG. 1), of flexible conduit 60. Cam section 69 projects upwardly from a lever arm 74 and overlies passageways 72 and 73, and cam section 70 projects downwardly from the lever arm and overlies passageways 71 and 72. The back of holder 62 which faces the rear side of the flexible conduit 60 is preferably formed with a pair of ribs 76, 78 straddling the pivot point 68 of lever 74 as shown particularly in FIG. 13.

The device illustrated in FIGS. 11–14 may be used as follows:

If a maximum flow rate is desired, lever 74 is pivoted to its horizontal position as illustrated in FIG. 13, whereupon a low face 75 between the two cam sections 69 and 70 is aligned with flexible conduit 60, so that neither cam section 69 or 70 closes any of the three passageways 71, 72, 73. If a restricted rate, e.g. 60 ml/hr, is desired, lever 74 is pivoted to its upper position, as illustrated in FIGS. 12 and 14, whereupon cam section 69 closes both passageways 72 and 73, thereby leaving only passageway 71 open, producing the desired flow rate; this flow rate is indicated by indicia carried on the face of lever 74 viewable to the user in this position of the lever. On the other hand, if the third flow rate is desired, lever 74 is pivoted to its downward position, whereupon cam section 70 closes passageways 71 and 72, leaving only passageway 73 open, to produce the flow rate corresponding to that passageway.

In all of the above-described embodiments, each of the restrictor pins receivable in its respective passageway of the flexible conduit is formed with a metering slit (e.g. 16', 18', FIG. 1) for metering the flow through its respective passageway.

The Embodiment of FIGS. 15–16a

FIGS. 15, 16 and 16a illustrate a variation wherein the device includes a rigid metering collar 80 (FIG. 15) integrally formed with a plurality of tubular sleeves 81, 82, 83 interposed between the inlet connector 84 (FIG. 16) and the flexible conduit 90 formed with the three passageways 91, 92, 93. Inlet connector 84 carries a pair of metering pins 86, 88, but these pins are not formed with metering slits, corresponding to slits 16', 18' in FIG. 1 for example; rather, the rigid tubular sleeves 81, 83 receiving these pins are formed with metering recesses 81', 83' along their inner faces, as shown particularly in FIG. 16a, so as to meter the flow of the fluid to and through their respective passageways 91 and 93.

The arrangement illustrated in FIGS. 15, 16 and 16a better assures the non-obstruction of the metering passageways under various handling conditions, since these metering passageways are formed between two rigid surfaces (rigid pins 86, 88 received within rigid tubular sleeves 81, 83, respectively), rather than between a rigid member and a flexible member as in the previously described arrangements.

The Embodiment of FIG. 17

FIG. 17 illustrates a liquid transfusion system including an infusion bag 100 gravity feeding the infusion liquid to the infusion needle 102 via a transfusion line 104 having a drip chamber 106 and a flow control device 108 according to any of the described embodiments. To produce the desired fixed flow rate selected by manipulating the control member of the flow control device as described above, a colored marker strip 110 is wrapped around the transfusion line 104 at the location indicating the point 112 at which the infusion bag 100 should be suspended above the infusion point to produce the proper head for the selected fixed flow rate.

While the invention has been described with respect to several preferred embodiments, it will be appreciated that many variations may be made. For example, the flexible conduit could include only two passageways, or four or more passageways, to provide a smaller or larger number of fixed flow rates that may be preselected. Also other forms of restrictors could be used. Many other variations, modifications and applications of the invention may be made.

What is claimed is:

1. A fluid flow control device connectable in a line for controlling the flow of fluid therethrough, comprising:
    an inlet connector and an outer connector;
    a flexible conduit defining at least three passageways in side-by-side relation extending in parallel between said inlet and outlet connectors to provide at least three parallel paths for the flow of the fluid therebetween;
    one of said passageways having a full, unrestricted flow rate;
    a restrictor in each of the other two passageways for restricting the flow therethrough according to fixed predetermined rates lower than that of said one passageway;
    a pivotable clamp receiving said flexible conduit and having a cam member shaped such as to close the center passageway and one end passageway in one pivoted position, the center passageway and other end passageway in another pivoted position, and to open all said passageways in a third pivoted position;
    said pivotable clamp having a lower arm carrying indicia markings identifying the flow rate of the device according to the pivoted position of the lever arm.

2. The device according to claim 1, wherein each of said restrictors includes a pin carried by said inlet connector and receivable in a rigid tubular sleeve formed in a metering collar interposed between said inlet connector and said conduit, each of said tubular sleeves being received in its respective passageway of the flexible conduit and being formed with a metering recess on its inner face for metering the flow through its respective passageway.

3. A liquid transfusion apparatus comprising:
a transfusion line connectable to a supply of transfusion liquid;
a drip chamber connected in said transfusion line;
and a fluid flow control device connected in said transfusion line upstream of said drip chamber;
said fluid control device comprising:
an inlet connetor and an outlet connector;
a flexible conduit defining at least two passageways extending in parallel between said inlet and outlet connectors to provide at least two parallel paths for the flow of the fluid therebetween;
one of said passageways having a full, unrestricted flow rate;
a restrictor in at least one other of said passageways for restricting the flow therethrough according to a fixed predetermined rate lower than that of said one passageway;
and a manually manipulatable control member having a normal position opening both of said passageways to produce a normal full flow, and at least one restricted position for closing said one passageway having a full, unrestricted flow rate to produce a flow of the fluid from said inlet connector to said outlet connector according to said predetermined restricted rate;
said transfusion line including a marker at the location thereof indicating the point at which the supply of transfusion liquid should be suspended about the infusion point to produce the proper head for the selected fixed flow rate.

* * * * *